United States Patent
Barnhorst et al.

(10) Patent No.: US 6,680,392 B1
(45) Date of Patent: Jan. 20, 2004

(54) PROCESS FOR REMOVING POLYSORBITOLS FROM SORBITAN ESTERS

(75) Inventors: Jeff A. Barnhorst, Cincinnati, OH (US); Dean A. Oester, Cincinnati, OH (US)

(73) Assignee: Cognis Corporation, Ambler, PA (US)

( * ) Notice: Subject to any disclaimer, the term of this patent is extended or adjusted under 35 U.S.C. 154(b) by 834 days.

(21) Appl. No.: 08/946,087

(22) Filed: Oct. 7, 1997

(51) Int. Cl.$^7$ ............................................. C07D 307/02
(52) U.S. Cl. ........................................................ 549/478
(58) Field of Search ........................................ 549/478

(56) References Cited

U.S. PATENT DOCUMENTS 4,297,290 A * 10/1981 Stockburger ................ 549/478
5,306,831 A 4/1994 Beshouri et al. ............ 549/478

OTHER PUBLICATIONS

Aldrich Chemical Co., Inc. (1996), p. 1344.*

* cited by examiner

Primary Examiner—J. Parsa
(74) Attorney, Agent, or Firm—John E. Drach; Steven J. Trzaska

(57) ABSTRACT

A process for removing polyol impurities from a sorbitan ester solution involving: (a) providing a sorbitan ester solution containing polyol impurities; (b) adding to the sorbitan ester solution a clarifying-effective amount of a silica component; (c) adsorbing the polyol impurities from the sorbitan ester solution onto the silica to form a mixture of sorbitan ester and polyol-containing silica; and (d) removing the polyol-containing silica from the sorbitan ester solution.

9 Claims, No Drawings

PROCESS FOR REMOVING POLYSORBITOLS FROM SORBITAN ESTERS

FIELD OF THE INVENTION

The present invention generally relates to an improved process for removing polysorbitols from sorbitan esters. More particularly, the invention relates to the use of silica to remove polysorbitols from sorbitan ester solutions.

BACKGROUND OF THE INVENTION

Sorbitan fatty acid esters have wide spread utility in many areas as an emulsifying agent in the formation of both water-in-oil and oil-in-water emulsions. Generally, sorbitol and a fatty acid, or a combination of fatty acids are reacted at a temperature greater than about 200° C., under a flow of inert gas, in the presence of an acidic or basic catalyst, to produce sorbitan fatty acid esters. A combination of mono-, di-, tri-, and tetra-esters of sorbitan as well as impurities such as polyols formed by the self-condensation of sorbitan molecules, unreacted sorbitans and isosorbides are produced from this process. These impurities are also present in the commercial sorbitan ester products.

It has been found that these polysorbitol impurities tend to form an undesirable sludge during an emulsifying process. Therefore, it is desirable to remove these impurities from the sorbitan fatty acid esters, after their production via esterification, in order to avoid the undesirable production of sludge.

Previous methods of extracting these impurities from the sorbitan ester mixtures have involved the dissolution of the sorbitan esters into a solvent, treatment with an aqueous metal salt to form separate phases, i.e., organic and aqueous, followed by separation of the organic phase from the aqueous phase.

Another method involves allowing these polyol impurities to settle out of the sorbitan ester mixture, over a prolonged period of time, followed by their removal from the bottom of the esterification reactor.

SUMMARY OF THE INVENTION

The present invention is directed to a process for removing polyol impurities from sorbitan ester solutions involving:

(a) providing a sorbitan ester solution containing polyol impurities;

(b) adding to the solution from about 0.01 to about 10% actives, based on the total weight of the final crude ester product, of a silica component;

(c) adsorbing the polyol impurities onto the silica component to form a mixture of polyol-containing silica and sorbitan ester; and (d) filtering the polyol-containing silica from the sorbitan ester solution.

DESCRIPTION OF THE INVENTION

Other than in the operating examples, or where otherwise indicated, all numbers expressing quantities of ingredients or reaction conditions are to be understood as being modified in all instances by the term "about".

It has surprisingly been discovered that sorbitan ester solutions can be rid of polyol impurities contained therein, such as isosorbides and polysorbitols, thereby rendering the resultant sorbitan ester solution clear in appearance, by the addition of a clarifying-effective amount of a silica component. During the esterification of sorbitols with fatty acids to form sorbitan esters, the unreacted sorbitols have a tendency to self-condense, thereby forming a type of sugar polymer/impurity. The presence of these impurities in the sorbitan ester solution causes the sorbitan esters to appear hazy/cloudy.

Suitable sorbitan esters which may be clarified by the process of the present invention are those corresponding to formula I:

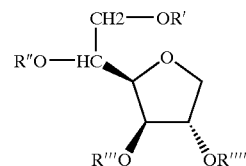

wherein R', R",R'" and R"" may be, indvidually,

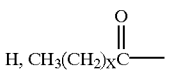

wherein x is an integer form 0–2 an unsaturated fatty acid such as oleate, linoleate, patmitoleate, myristoleate.

Examples of suitable sorbitan esters which may be clarified by the process of the present invention include, but are not limited to, sorbitan sesquioleate, sorbitan trioleate, sorbitan monooleate, sorbitan monopalmitate, sorbitan monostearate and sorbitan tristearate.

Suitable silicas which may be employed in the process of the invention include, but are not limited to, crystalline, amorphous, hydrous and anhydrous.

The term amorphous, when used to describe silica, denotes a lack of crystalline structure, as defined by x-ray diffraction. Some short-range organization may be present and is indicated by electron-diffraction, but this ordering gives no sharp x-ray diffraction pattern. Silica can be either hydrated, i.e., up to ca 14%, or anhydrous. The chemical bonding in amorphous silica is of several types, including siloxane (—Si—O—Si), silanol (Si—O—H), and at the surface, silane (Si—H) or organic silicon (—Si—O—R or —Si—C—R).

Silica gel is a coherent, rigid, continuous three-dimensional network of spherical particles of colloidal silica. Silica gels are classified into three types: regular density gel, intermediate-density gel, and low-density gel. Silica powder can be made by grinding or micronizing dried gels, which decreases the size of the gel fragments but leaves the ultimate gel structure unchanged. Gels and powders are characterized by the density, size, and shape of the particles, particle distribution, and by aggregate strength or coalescence.

When silica is used as an adsorbent, the pore structure determines the gel-adsorption capacity. Pores are characterized by specific surface area, specific pore volume (total volume of pores per gram of solid), average pore diameter, pore-size distribution, and the degree to which entrance to larger pores is restricted by smaller pores.

While all of the above-disclosed silica types possess some polyol-removal capabilities, a particularly preferred silica is a hydrated amorphous silica, preferably in powder form. A commercial example of a preferred silica is BRITESORB® PM 5108 Hydrous Silica, available from PQ Corp.

For convenience, the inventive process will be described in terms of its preferred embodiment, in which a hydrated amorphous silica is employed. In a typical process, sorbitol and fatty acid esters are esterified in a reactor, in the presence of a catalyst. Since the processes by which sorbitan esters are formed is well known in the art, the particulars regarding their formation need not be addressed herein. Once the esterification reaction is complete, a solution containing sorbitan esters and polyol impurities is formed. To this solution there is then added, with agitation, and at a temperature of from about 30° C. to about 80° C., and preferably at from about 50° C. to about 70° C., from about 0.01 to about 10% actives, and preferably about 1% actives, based on the total weight of the final crude ester product formed, of a hydrated amorphous silica. The hydrated amorphous silica is allowed to adsorb the polyol impurities from the sorbitan ester solution, while under agitation, for a period of from about 20 to about 60 minutes, and preferably about 30 minutes, resulting in the formation of a polyol-containing silica dispersed in the sorbitan ester solution.

The silica was found to rapidly adsorb polyol impurities from the sorbitan ester solution, rendering the purified sorbitan ester solution, after filtration, clear in appearance. By employing the hydrated amorphous silica to remove polyol impurities from the reaction mixture, the downtime associated with the previous process which involved waiting for these impurities to settle out of the reaction mixture, was significantly shortened from about 8 hours to about 30 minutes.

The polyol-containing silica is then removed from the sorbitan ester reaction solution by any conventional filtration means. One example thereof involves passing the sorbitan ester reaction solution containing the polyol-containing silica dispersed therein through a filtration apparatus which simultaneously collects the polyol-containing silica while allowing the clarified sorbitan ester solution to pass through. Any known filtration apparatus capable of collecting solid particles may be employed such as, for example, a plate and frame press.

A plate and frame press apparatus filters product in the following way. The crude product, in this case the mixture of polyol-containing silica and sorbitan ester, enters a precoat tank attached to the end of a press. At the bottom of the precoat tank is a pipe going to a pump located under the press. The pump sucks the crude product out of the precoat tank and forces the crude product into the plate and frame section of the press. The plate is covered on both sides by filter paper. The product is forced inside the plate through a hole in the bottom of the plate. Then the material is forced through the paper and onto the frame which has channels on it to take the clean product out to the other side of the plate. The plate has two holes, one on the bottom right (crude), the other on the top left (clean). A plate and frame press apparatus can have from 1–20 plates and frames.

Another common filtration apparatus which may be used to remove the polyol impurities from sorbitan ester solution is a centrifuge. Centrifugation is a separation technique based on the application of centrifugal force to a mixture or suspension of materials.

The present invention will be better understood from the examples which follow, all of which are illustrative only and are not meant to unduly limit the scope of the invention in any way.

EXAMPLES

A sorbitan monooleate was prepared by charging a reactor with 40% by weight of a sorbitol, 60% by weight of oleic acid, and 0.25% by weight sodium hydroxide acting as a catalyst. Once the reaction process is complete, the resultant sorbitan monooleate solution is cooled to about 65° C. A hydrous silica, commercially available under the name BRITESORB®, was then added to the cooled sorbitan monooleate solution in an amount of 1% by weight, based on the total weight of the solution in the reactor after an acid value of 2 was reached. The sorbitan monooleate and hydrous silica mixture was then mixed for 30 minutes to allow the polyol impurities to be adsorbed by the silica, after which the impurities were immediately pressed off. The final sorbitan monooleate ester product was clear in appearance.

COMPARATIVE EXAMPLE

A sorbitan monooleate was prepared, per the above-disclosed process. Once the acid value of the resultant sorbitan monooleate solution was adjusted to the desired level, the polyol impurities contained therein were removed by allowing them to settle out of the solution over a period of 10 hours.

As can be seen from the above-disclosed data, by employing the process of the present invention to remove polyol impurities from sorbitan esters, the downtime associated with their removal is significantly decreased.

What is claimed is:

1. A process for removing polyol impurities from a sorbitan ester solution comprising:
   (a) providing a sorbitan ester solution containing polyol impurities;
   (b) adding to the sorbitan ester solution from about 0.01 to about 10% actives, based on the total weight of final crude ester product formed, of a silica component at a temperature of from about 30° to about 80° C.;
   (c) mixing the sorbitan ester solution and silica component;
   (d) adsorbing the polyol impurities from the sorbitan ester solution onto the silica to form a mixture of polyol-containing silica and sorbitan ester; and
   (e) removing the polyol-containing silica from the sorbitan ester solution.

2. The process of claim 1 wherein about 1% actives of the silica component, based on the total weight of final crude ester product, is added to the sorbitan ester solution.

3. The process of claim 1 wherein the silica component is a hydrated amorphous silica powder.

4. The process of claim 1 wherein the sorbitan ester is selected from the group consisting of sorbitan sesquioleate, sorbitan trioleate, sorbitan monooleate, sorbitan mononopalmitate, sorbitan monostearate and sorbitan tristearate.

5. The process of claim 1 wherein the polyol impurities are adsorbed onto the silica for a period of from about 20 to about 60 minutes.

6. The process of claim 1 wherein the polyol-containing silica is removed from the sorbitan ester solution using a filtration apparatus.

7. The process of claim 6 wherein the filtration apparatus is a plate and frame press.

8. The process of claim 5 wherein the polyol impurities are adsorbed onto the silica for a period of about 30 minutes.

9. The process of claim 4 wherein the sorbitan ester is sorbitan monooleate.

* * * * *